United States Patent [19]
Nichols et al.

[11] Patent Number: 5,843,099
[45] Date of Patent: Dec. 1, 1998

[54] SINGLE SYSTEM LIGATURE CARRIER AND TISSUE CLAMP FOR SACROSPINOUS COLPOPEXY

[75] Inventors: David H. Nichols, Providence, R.I.; Dionysios K. Veronikis, Watertown, Mass.

[73] Assignee: BEI Medical Systems, Inc., Teterboro, N.J.

[21] Appl. No.: 784,766

[22] Filed: Jan. 16, 1997

[51] Int. Cl.[6] ..................................................... A61B 17/04
[52] U.S. Cl. .......................... 606/144; 606/145; 606/147; 606/148
[58] Field of Search ................................... 606/139, 144, 606/145, 147, 148, 151

[56] References Cited

U.S. PATENT DOCUMENTS

| | | | |
|---|---|---|---|
| 1,545,682 | 7/1925 | Nelson | 606/139 |
| 2,213,830 | 9/1940 | Anastasi | 606/145 |
| 2,286,578 | 2/1942 | Sauter | 128/340 |
| 4,161,951 | 7/1979 | Scanlan, Jr. | 128/340 |
| 4,373,530 | 2/1983 | Kilejian | 128/334 R |
| 5,059,201 | 10/1991 | Asnis | 606/144 |
| 5,181,919 | 1/1993 | Bergman et al. | 606/144 |
| 5,507,756 | 4/1996 | Hasson | 606/139 |
| 5,522,820 | 6/1996 | Caspari et al. | 606/148 |

*Primary Examiner*—Michael Powell Buiz
*Assistant Examiner*—Tina T. D. Pham
*Attorney, Agent, or Firm*—Allen A. Dicke, jr.

[57] ABSTRACT

The single system ligature carrier and tissue clamp for sacrospinous colpopexy has an elongated body with a fixed handle on its proximal end. An additional movable handle is connected to a movable clamp jaw and a needle jaw on its distal end so that, at a distance, tissue can be engaged and pierced with a needle facilitated by clamp fingers passing a suture therethrough, as well as clamping and securing the embraced tissue. The positioning, clamping and suture penetration are accomplished by a single instrument.

15 Claims, 3 Drawing Sheets

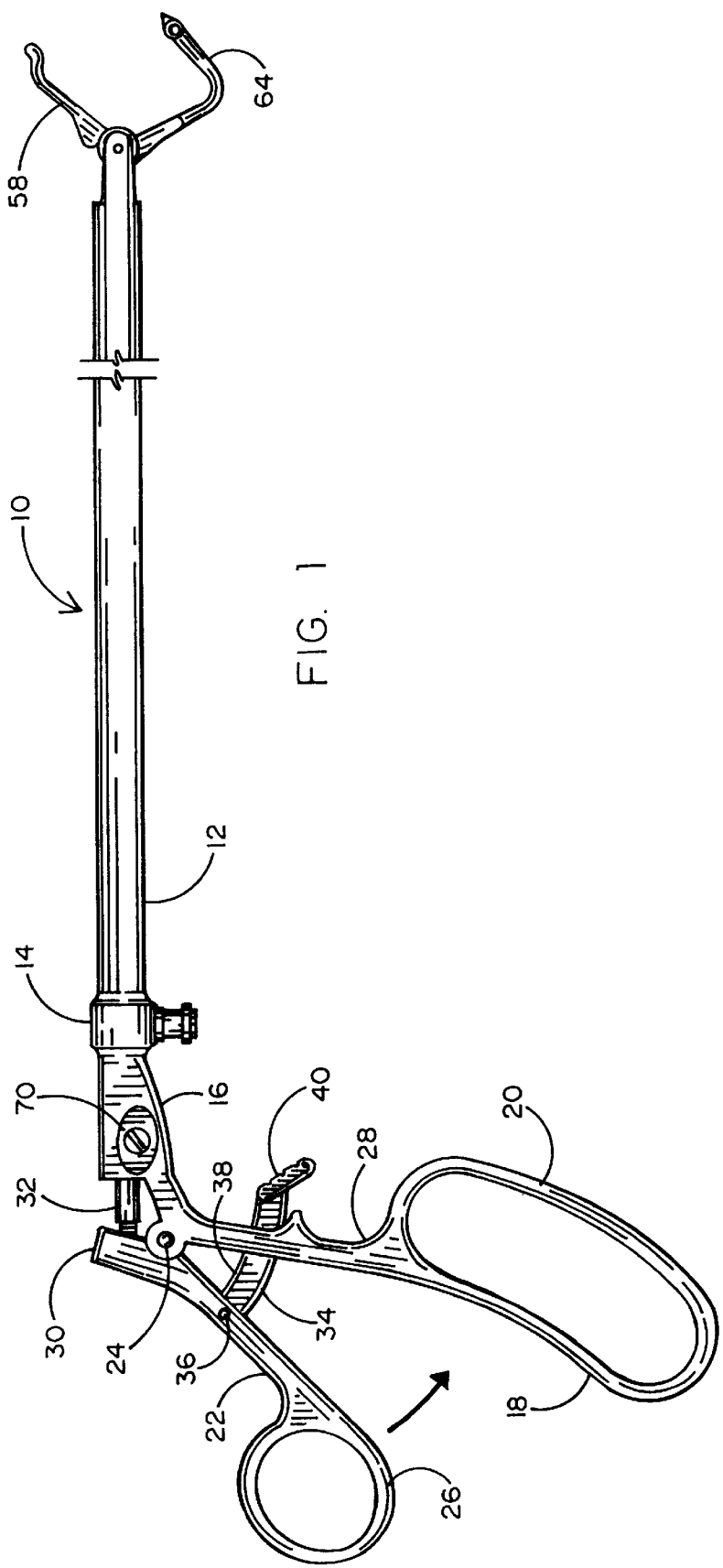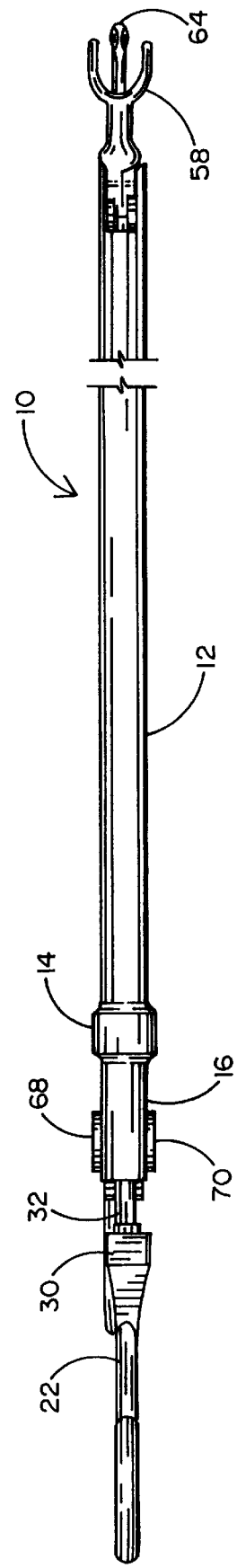

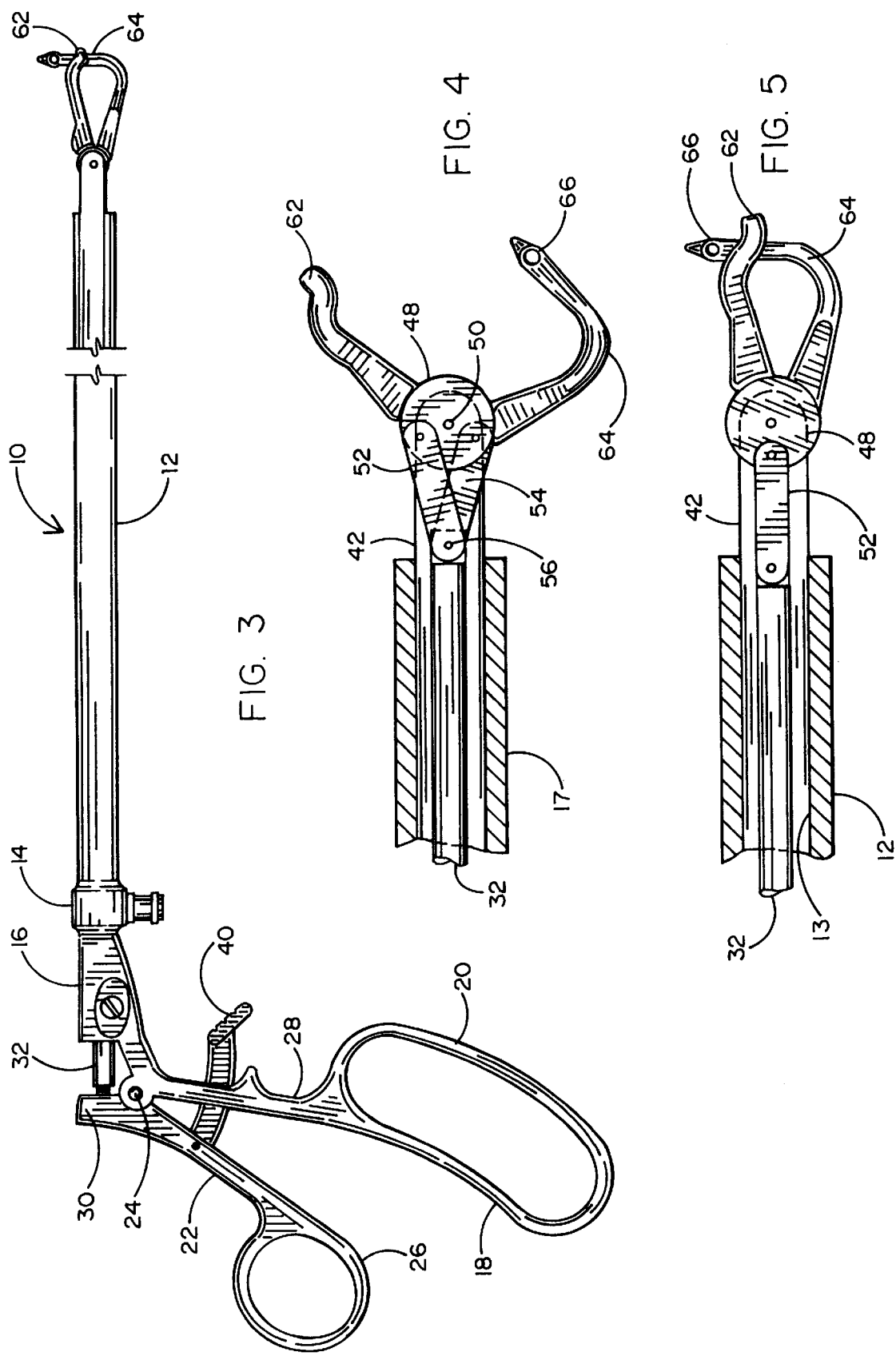

SINGLE SYSTEM LIGATURE CARRIER AND TISSUE CLAMP FOR SACROSPINOUS COLPOPEXY

FIELD OF THE INVENTION

The ligature carrier is especially configured to clamp tissue and pass a needle with suture through the comprised tissue in a single mechanical motion. This is desirable in deep surgical exposure where the surgeon's hand rotations are cumbersome, such as during sacrospinous colpopexy. The instrument accomplishes tissue clamping, needle penetration and simultaneous ligature positioning.

BACKGROUND OF THE INVENTION

The only unifying principle bridging all disciplines of surgery is the utilization of suture and suturing techniques to suspend and/or approximate tissue in order to promote healing, regardless of whether the approximated tissue is bone or a large vessel sutured to a graft. The passage of the suture through the tissue is performed by the surgeon in a multistep process requiring several instruments and surgical movement. These include grasping the required tissue with an instrument, penetration of the tissue usually with a needle and attached suture and recovery of the needle on the other side of the tissue. The needle is driven through the tissue by a needle driver which firmly holds the needle in a fixed position. The surgeon, by applying pressure and rotating the hand holding the needle driver and encompassed needle, penetrates the tissue. Usually, recovery of the needle is performed by the same needle driver, occasionally by the tissue forceps and sometimes by a separate second needle driver, especially in areas of limited surgical exposure.

Alternative techniques have combined the needle driver and needle, but still require hand rotations and/or concomitant back pressure for the needle to penetrate the desired tissue. Additionally, the instruments are open-ended, not containing the desired tissue until the suture can be retrieved. This causes the loss of the penetrated tissue. When operating in areas of limited exposure and at a distance from the body surface, retraction by assistants is crucial. A small amount of blood obscures the surgical field, and recovery of needles and sutures may be lost by small movements. This is especially true during deep pelvic surgery, such as transvaginal sacrospinous colpopexy.

Techniques for transvaginal sacrospinous colpopexy have been accomplished by a variety of suturing methods, such as the open-ended ordinary curved suturing needle manipulated by clamps and forces, as well as other open-ended non-tissue-securing ligature-carrying instruments. All require the surgeon to identify the anatomy by palpation and to place, force and rotate or elevate the instruments in limited surgical exposure, most frequently without direct surgical visualization of the passage of the needle through the tissue.

The limited space deep in the pelvis, around nerves and arteries, make it difficult to perform the standard surgical suturing steps of positioning, clamping, needle/suture penetration under direct surgical vision at some distance and through an incision in the posterior vagina consistently and safely, especially when they are performed by separate instruments not designed to function in limited surgical exposure and at a significant distance from the body surface.

SUMMARY OF THE INVENTION

In order to aid in the understanding of this invention, it can be stated in essentially summary form that the instrument is a combination tissue clamp and automatic/mechanical needle driver and ligature carrier which is particularly useful for suturing in difficult or limited surgical exposure areas such as during sacrospinous colpopexy. The ligature carrier/clamp instrument has an elongated body and inter-engaging jaws on the distal end. One jaw (the lower) is slender and perforated to carry a ligature(s), and the upper jaw has two spaced fingers opposite the slender perforated digit. The upper jaw functions to compress and push the tissue past the perforation of the lower jaw. This freely movable dual action, integrated movement of the lower digit and upper digit enables the encompassed tissue to be ligated and secured by concomitant clamping within the space inside the digits. Concomitantly, the tissue is compressed below the perforation, which enables suture retrieval. At this point, the instrument can be completely out of the hands of the surgeon without losing the ligated tissue. This is easily accomplished at a distance due to the elongated cylindrical slender body. No surgical rotations or elevations are required which may obscure vision because an anterior handgrip provides positioning and, by squeezing the handgrip, the lower and upper digits simultaneously and concomitantly close around the tissue ligating, securing and clamping. The surgeon merely places the tip of the lower digit next to the tissue and the curvilinear path of the lower digit penetrates the tissue as the handgrip is squeezed. Concomitantly, the upper digit advances the tissue over the lower digit facilitating suturing while securing and clamping the "bite" of tissue.

It is, thus, a purpose and advantage of this invention to provide an instrument with tissue-securing properties, as well as having ligature carrier properties for sacrospinous colpopexy wherein ligature positioning, tissue clamping and ligature perforation can be accomplished with a single elongated instrument to maximize surgical visual observation and limit surgical hand movements within the confines of limited surgical access.

It is a another purpose and advantage of this invention to provide an instrument with clamping and ligature carrier properties which is especially useful for sacrospinous colpopexy wherein the ligature is threaded into a perforated jaw which is opposed by a clamping jaw having clamping digits so that, upon positioning, tissue clamping is concomitant with tissue perforation by the ligature, without the need for multiple instruments, to permit accurate placement and secure clamping during suturing in one surgical maneuver.

Other purposes and advantages of this invention will become apparent from a study of the following portion of the specification, the claims and the attached drawings.

BRIEF DESCRIPTION OF THE DRAWINGS

FIG. 1 is a side-elevational view of the ligature carrier/clamp of this invention for sacrospinous colpopexy in the open position.

FIG. 2 is a plan view thereof.

FIG. 3 is a view similar to FIG. 1 showing the ligature carrier/clamp in the closed position.

FIG. 4 is an enlarged view of the distal end of the ligature carrier/clamp in the open position, with parts broken away and parts taken in section.

FIG. 5 is a view similar to FIG. 4, showing the ligature carrier/clamp in the closed position.

DESCRIPTION OF THE PREFERRED EMBODIMENTS

Figure 6:
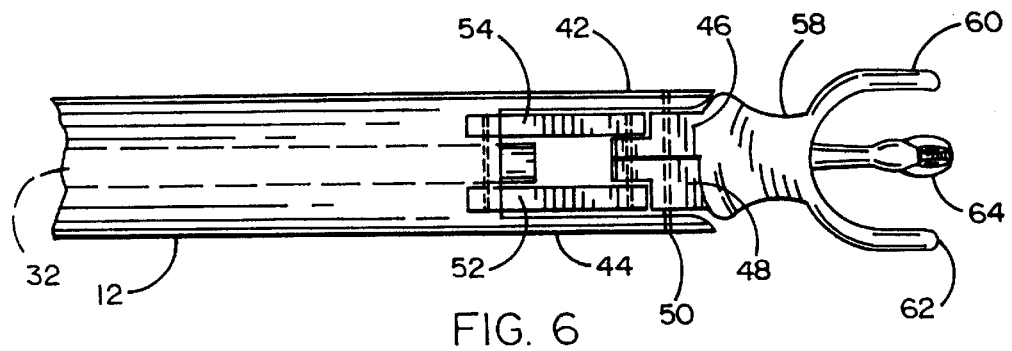
FIG. 6 is a plan view of the ligature carrier/clamp, as seen in FIG. 5.
Figure 7:
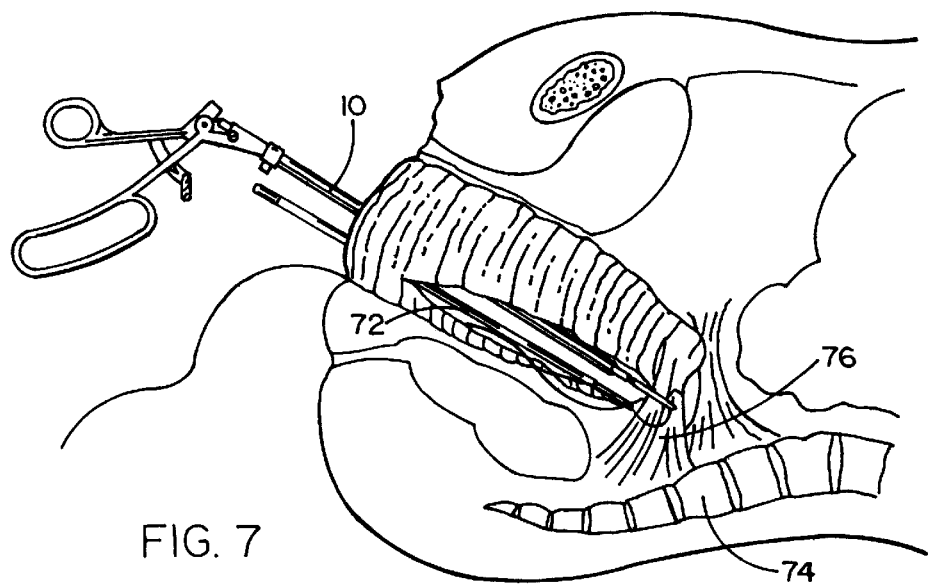
FIG. 7 is a perspective view of the ligature carrier/clamp together with a female pelvic section showing the ligature carrier/clamp positioned for suture installation.
Figure 8:
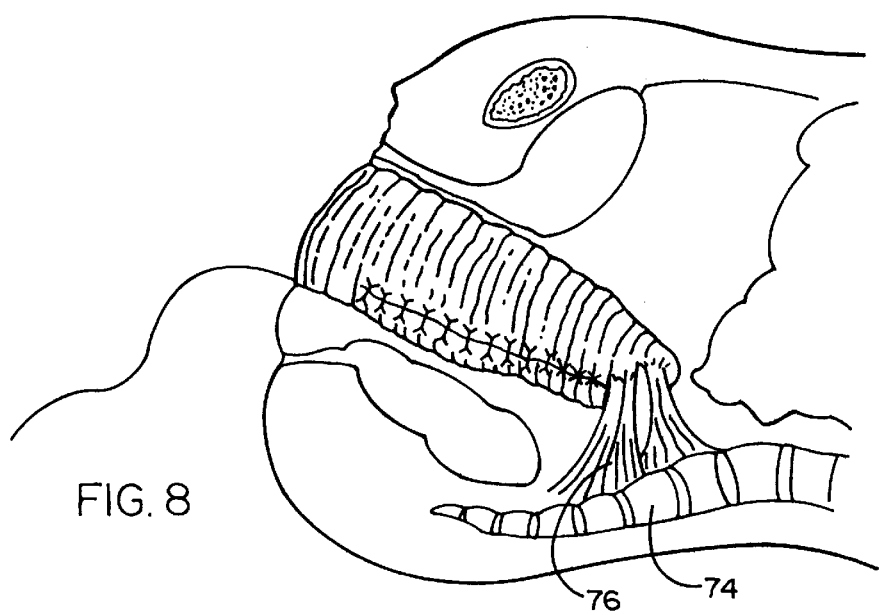
FIG. 8 is a view similar to FIG. 7 showing the completed procedure.

The ligature carrier/clamp of this invention is generally indicated at 10 in FIGS. 1, 2, 3 and 7. The ligature carrier/clamp 10 has an elongated body 12 which is in the form of a circular cylindrical tube, as seen in FIGS. 4 and 5. It has an opening 13 therethrough. The proximal end of the elongated body has a boss 14 into which the tube 12 is secured. Handle body 16 carries the boss 14 as an integral portion thereof. Depending from the handle body is fixed handle 18, which has a finger loop 20 for manual grasp for manual positioning control of the ligature carrier/clamp.

Movable handle 22 is pivoted on the juncture between the handle body and the fixed handle on pivot pin 24. The movable handle has a thumb loop 26 thereon. With the thumb in the thumb loop, the index finger in recess 28 and the three remaining fingers in finger loop 20, the ligature carrier/clamp 10 can be accurately manipulated and operated with one hand from the surgeon's palm as an extension of the arm. Lever 30 is part of movable handle 22 and extends above pivot pin 24. Operating rod 32 is attached to the handle so that it is actuated back and forth within body 12 by means of motion of the movable handle. A convenient attachment of the operating rod to the lever 30 is by means of a ball on the proximal end of the operating rod being engaged in a ball-shaped slot extending downward in lever 30. Such a structure provides the necessary degrees of freedom while constraining the rod to axial movement with rotation of lever 30 around its pivot pin 24.

Latch 34 is pivotally mounted on its pivot pin 36 in movable handle 22. The latch passes through a slot in fixed handle 18 and is spring-loaded in the upward direction, as seen in FIGS. 1 and 3. Notch 38 is formed in the top edge of the latch 34. When the movable handle 22 moves to the closed position shown in FIG. 3, the notch 38 engages on a stop in the slot in the movable handle. The spring urging the latch 34 in the upward direction retains the latch in the upward, latched position shown in FIG. 3. This allows the clamped/ligated tissue to remain contained and permits the surgeon the freedom of both hands. Finger pad 40 is conveniently positioned for the index finger in recess 28 to reach up and release the latch from its locked position when desired.

The distal end of the elongated tubular body 12 is slotted in the up-and-down direction to form side panels 42 and 44. In FIGS. 4 and 5, the near side panel 44 is cut away, but the far side panel 42 can be seen extending beyond the slotted portion. Discs 46 and 48 are mounted on pivot pin 50 to be rotatable between the side panels. Connecting rods 52 and 54 have their proximal ends pivoted on the same pivot pin 56 through operating rod 32 adjacent its distal end. The outer ends of the connecting rods 52 and 54 are respectively pivotally connected to discs 48 and 46. Clamp jaw 58 is mounted on disc 46. The clamp jaw 58 carries clamp fingers 60 and 62. The disc 48 carries a slender jaw in the form of perforated needle 64. As seen in FIGS. 3, 4 and 5, the fingers of the clamp jaw extend substantially radially outward on the jaw, while the needle 64 extends substantially radially outward and then has a bend therein so that it extends in a generally circumferential direction.

The end of the needle 64 has an eye 66, see FIG. 4, through which a suture can be threaded. The configuration of the clamp jaw with its fingers and the jaw with the needle is such that, in the open position, there is space therebetween and the needle point the clamp fingers, as seen in FIG. 4. The space is sufficient to be able to engage over and clamp the desired tissues, as described below. The upwardly directed portion of the needle beyond the bend reaches beyond the fingers 60 and 62 in the closed position, as seen in FIGS. 3 and 5. The eye 66 is thus above the fingers of the jaw so that a suture therethrough can be engaged. The suture threaded through the eye 66 can be secured on its proximal end by wedging it under one of the suture wedges 68 or 70.

In use, suitable clamps are placed on the edge of the vagina to serve as a guide and to maintain adequate orientation. A V-shaped incision 72 is made in the perineum. Space is developed by incising the posterior vaginal wall longitudinally with two parallel incisions until the vaginal apex is reached. To perform a right sacrospinous colpopexy, the right index finger of the surgeon identifies the ischial spine and notes the position of the spine and the size of the coccygeus/sacrospinous ligament complex. Direct adequate illumination permits visualization of the superior surface of the coccygeus muscle and underlying sacrospinous ligament 76 running posteromedially from the ischial spine. When the right coccygeus/sacrospinous ligament complex is to be used, the middle finger of the left hand is placed on the medial surface of the ischial spine. The ligature carrier/clamp 10 has been previously loaded with one or more monofilament or braided sutures. In the usual case for the right sacrospinous colpopexy, the two loaded sutures are threaded through the eye 66 of the needle 64 from left to right. The left suture wedge 68 of the ligature carrier/clamp secures both of the suture ends close to the left of the instrument handle to avoid contamination. The sutures from left to right traverse past the eye of the needle for only three or four inches. This short retrieval end facilitates retrieval of the sutures on the right side of the instrument.

The ligature carrier/clamp 10 is then brought into the operative field and, under direct vision, is positioned so that the lower needle jaw can penetrate the coccygeus/sacrospinous ligament complex at a point about two centimeters medial to the ischial spine. As the jaws are closed by moving the thumb loop, the tissue is first clamped between the needle tip and the fingers of the clamp jaw. The handle is squeezed to close the jaws, and this advances the needle tip through the tissue as the tissue is held by the fingers of the clamp jaw. The grasped tissue is held securely within the instrument by the closed position of the latch. In this state, the surgeon can visualize the tip of the ligature carrier/clamp, as well as the embraced tissue. At this point, a tug on the instrument with the jaws closed will demonstrate adequate purchase. When adequate purchase is demonstrated, the right side sutures are grasped by a suture hook and pulled through the sacrospinous ligament. The sutures are released from the left suture wedge. The instrument is opened and the ligature carrier/clamp is removed from the tissue. As it is being removed from the operative field, the sutures are concomitantly unthreaded from the eye of the needle.

If the width of the vaginal vault is sufficiently wide to reach between the ischial spines, the same procedure may also be accomplished on the opposite side of the pelvis to become a bilateral colpopexy. Alternatively, a left-handed surgeon may desire to proceed primarily on the left since the instrument is ambidextrous. The sutures are then sewn to the underside of the vagina at the vault. All sutures are tied, and the vaginal incision is also closed. In this way, a sacrospinous colpopexy is accomplished.

This invention has been described in its presently contemplated best embodiment, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A single system ligature carrier and tissue clamp for sacrospinous colpopexy comprising:

an elongated body having a proximal end and a distal end;

a clamp jaw pivotally mounted on said distal end of said elongated body, said clamp jaw carrying first and second fingers;

a needle jaw pivotally mounted on said distal end of said body, a needle on said needle jaw, said needle having a tip, a ligature opening through said needle adjacent said tip, said needle jaw being movably mounted with respect to said clamp jaw so that it is movable from a first position wherein said needle is away from said clamp jaw fingers to a second, closed position wherein said needle extends between said clamp jaw fingers and tissue can be clamped between said jaws, said ligature opening being on one side of said clamp jaw fingers in said first position and on the other side of said clamp jaw fingers in said second position, said needle jaw and said clamp jaw being sized to penetrate through the coccygeus muscle and engage around the sacrospinous ligament for engagement by a ligature; and a fixed handle on said proximal end to be engaged by some of the fingers of the user and a movable handle to be engaged by at least one other finger of the user, an operating rod extending from said movable handle to at least one of said jaws to move said needle with respect to said clamp jaw for moving said needle jaw with respect to said clamp jaw fingers from said first position to said second position and lock means for releasably locking said needle in said second position with respect to said clamp jaw fingers.

2. A single system ligature carrier and tissue clamp for sacrospinous colpopexy comprising:

an elongated body having a proximal end and a distal end;

a clamp jaw pivotally mounted on said distal end of said elongated body, said clamp jaw carrying first and second fingers;

a needle jaw pivotally mounted on said distal end of said body, a needle on said needle jaw, said needle having a tip, a ligature opening through said needle adjacent said tip, said needle jaw being movably mounted with respect to said clamp jaw so that it is movable from a first position wherein said needle is away from said clamp jaw fingers to a second, closed position wherein said needle extends between said clamp jaw fingers and tissue can be clamped between said jaws, said ligature opening being on one side of said clamp jaw fingers in said first position and on the other side of said clamp jaw fingers in said second position, said needle jaw and said clamp jaw being sized to penetrate through the coccygeus muscle and engage around the sacrospinous ligament for engagement by a ligature;

means on said proximal end of said body for moving said needle jaw with respect to said clamp jaw fingers from said first position to said second position; and lock means for releasably locking said needle in said second position with respect to said clamp jaw fingers.

3. The single system ligature carrier and tissue clamp for sacrospinous colpopexy of claim 2 wherein said lock means is on said proximal end of said body so as to be manually releasably by the user.

4. The single system ligature carrier and tissue clamp for sacrospinous colpopexy of claim 2 wherein said body is tubular and said operating rod passes through the tubular interior of said body and both said clamp jaw and said needle jaw are movably mounted on the distal end of said body.

5. The single system ligature carrier and tissue clamp for sacrospinous colpopexy of claim 4 wherein said distal end of said body is bifurcated and a pivot pin extends thereacross, both said clamp jaw and said needle jaw being pivoted on said pivot pin so that both said clamp jaw and said needle jaw are movably mounted with respect to said body, said operating means being connected to both said clamp jaw and said needle jaw so that upon actuation, said fingers of said clamp jaw and said needle jaw move toward each other.

6. A single system ligature carrier and tissue clamp for sacrospinous colpopexy comprising:

an elongated body having a proximal end and a distal end, said distal end of said body being bifurcated and a pivot pin extending thereacross;

a clamp jaw pivotally mounted on said pivot pin on said distal end of said elongated body, said clamp jaw carrying first and second fingers;

a needle jaw pivotally mounted on said pivot pin on said distal end of said body, a needle on said needle jaw, said needle having a tip, a ligature opening through said needle adjacent said tip, both said clamp jaw and said needle jaw being pivoted on said pivot pin so that both said clamp jaw and said needle jaw are movably mounted with respect to said body, from a first position wherein said needle is away from said clamp jaw fingers to a second, closed position wherein said needle extends between said clamp jaw fingers and tissue can be clamped between said jaws, said ligature opening being on one side of said clamp jaw fingers in said first position and on the other side of said clamp jaw fingers in said second position, said needle jaw and said clamp jaw being sized to penetrate through the coccygeus muscle and engage around the sacrospinous ligament for engagement by a ligature; and operating means on said proximal end of said body connected to both said clamp jaw and said needle jaw so that upon actuation, said fingers of said clamp jaw and said needle jaw move from said first position to said second position.

7. A single system ligature carrier and tissue clamp for sacrospinous colpopexy comprising:

an elongated body having a distal end and a proximal end;

a fixed handle secured to said proximal end of said elongated body, said fixed handle being configured for manual grasp to position said distal end of said elongated body;

a movable handle mounted on said proximal end for manual engagement and movement with respect to said fixed handle;

first and second clamp fingers on a clamp jaw which is movably mounted on said distal end of said elongated body, and a needle jaw movably mounted on said distal end of said elongated body, a needle on said clamp jaw, said needle having an eye, said needle being movable with respect to said clamp fingers from an open position wherein said needle is away from said clamp fingers to a closed position wherein said needle is positioned with its eye past said clamp fingers, said needle and said clamp fingers being sized and shaped to clamp coccygeus muscle and engage around the sacrospinous ligament to pass a ligature therearound;

connection means between said movable handle and said needle and said clamp fingers for moving said needle with respect to said fingers; and a latch for releasably latching said needle in its closed position to permit the surgeon to have both hands free to recover the suture.

8. The single system ligature carrier and tissue clamp for sacrospinous colpopexy of claim 7 wherein said latch is inter-engaged between said movable handle and said fixed handle and said latch is manually engageable so that it can be moved to an unlatched position and said needle can be moved from its second to its first position with respect to said finger.

9. The single system ligature carrier and tissue clamp for sacrospinous colpopexy of claim 7 wherein said elongated body is tubular and said means interconnecting said movable handle and said needle is an operating rod extending through said tubular body.

10. The single system ligature carrier and tissue clamp for sacrospinous colpopexy of claim 9 wherein both said needle and said clamp fingers are connected to be actuated by said operating rod so that in the open position, said needle is away from said clamp fingers and in the closed position, said needle extends between said clamp fingers.

11. The single system ligature carrier and tissue clamp for sacrospinous colpopexy of claim 7 wherein said means for moving is a movable squeeze handle mechanically connected to advance said needle on said distal and through the desired coccygeus muscle tissue in a curvilinear direction with simultaneous passage of suture through the tissue with concomitant advancing of said clamp jaw to press the desired tissue past the said needle eye.

12. The single system ligature carrier and tissue clamp for sacrospinous colpopexy of claim 7 wherein said needle eye is sized to permit the simultaneous passage of one or more sutures of virtually any standard size and configuration.

13. The single system ligature carrier and tissue clamp for sacrospinous colpopexy of claim 7 being configured to pass one or more sutures through coccygeus muscle tissue by a single instrument wherein said clamp jaw compresses and advances tissue over said needle jaw, said distal mounted needle jaw and said clamp jaw functioning as a tissue clamp securing the encompassed and ligated tissue by the said latch to permit the surgeon to have both hands free to recover the suture.

14. The single system ligature carrier and tissue clamp for sacrospinous colpopexy in accordance with claim 7 further including means at said proximal end of said elongated body for releasably retaining the ligature material.

15. The single system ligature carrier and tissue clamp for sacrospinous colpopexy in accordance with claim 14 wherein said means for engaging said suture material comprises a wedge on each side of said body adjacent to the proximal end of said body.

* * * * *